United States Patent
Wetterer et al.

(10) Patent No.: US 9,737,628 B2
(45) Date of Patent: Aug. 22, 2017

(54) HIGH-COVERAGE, LOW ODER MALODOR COUNTERACTANT COMPOUNDS AND METHODS OF USE

(71) Applicant: International Flavors & Fragrances Inc., New York, NY (US)

(72) Inventors: Sean M. Wetterer, Murray Hill, NJ (US); Drew T. Parkhurst, Yardley, PA (US); Richard Anthony Weiss, Livingston, NJ (US); Anthony T. Levorse, Jr., Westfield, NJ (US); Michael G. Monteleone, Hazlet, NJ (US); Richard M. Boden, Ocean, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 7 days.

(21) Appl. No.: 14/496,680

(22) Filed: Sep. 25, 2014

(65) Prior Publication Data

US 2016/0089469 A1  Mar. 31, 2016

(51) Int. Cl.
| | |
|---|---|
| *A61L 9/14* | (2006.01) |
| *A61L 2/00* | (2006.01) |
| *A61L 9/00* | (2006.01) |
| *A23G 4/06* | (2006.01) |
| *A23L 27/00* | (2016.01) |

(52) U.S. Cl.
CPC ............... *A61L 9/14* (2013.01); *A23G 4/06* (2013.01); *A23L 27/84* (2016.08); *A61L 2/00* (2013.01); *A61L 9/00* (2013.01); *A23V 2002/00* (2013.01)

(58) Field of Classification Search
CPC ........................................................ A61L 9/14
See application file for complete search history.

(56) References Cited

U.S. PATENT DOCUMENTS 4,420,423 A * 12/1983 Boden .................. C11B 9/0007
510/101

FOREIGN PATENT DOCUMENTS

WO    WO 0051560 A1 *  9/2000
WO    WO 2005046632 A2 *  5/2005

OTHER PUBLICATIONS

Merriam-Webster. "Confectionary." (c) 2013. Available from: < http://www.merriam-webster.com/dictionary/confectionary >.*
Kamboka, H., et al. "Components of Essential Oil from the Root of Glycyrrhiza glabra." J. Agricult. Chem. Soc. (1987), vol. 61, pp. 1119-1121.*
Greenberg, M., et al. "Compressed Mints and Chewing Gum Containing Magnolia Bark Extract are Effective against Bacteria Responsible for Oral Malodor." Journal of Agricultural and Food Chemistry. (2007), vol. 55, pp. 9465-9469.*
Obata, Y., et al. "Effect of synthesized cyclohexanol derivatives using L-menthol as a lead compound on the percutaneous absorption of ketoprofen." International Journal of Pharmaceutics. (2000), vol. 198, pp. 191-200.*
American Chemical Society. STN Database. RN 1497420-94-6.*
Mitsos, C. "Isosteres in Medicinal Chemistry." (c) 2006. Available from: < http://www.scripps.edu/baran/images/grpmtgpdf/Mitsos_Feb_06.pdf >.*

* cited by examiner

*Primary Examiner* — Noble Jarrell
*Assistant Examiner* — John S Kenyon
(74) *Attorney, Agent, or Firm* — Martin Zhang; XuFan Tseng; Elizabeth M. Stover

(57) ABSTRACT

A composition containing a malodor counteracting compound and a method for using the compound for counteracting a malodor in air space or a substrate is provided.

12 Claims, No Drawings

HIGH-COVERAGE, LOW ODER MALODOR COUNTERACTANT COMPOUNDS AND METHODS OF USE

BACKGROUND

Malodors are offensive odors, which are encountered in the air and on many substrates such as fabrics, hard surfaces, skin, and hair. Amines, thiols, sulfides, short chain aliphatic and olefinic acids, e.g., fatty acids, are typical of the chemicals found in and contributed to sweat, household, and environmental malodors. These types of malodors typically include indole, skatole, and methanethiol found in toilet and animal odors; piperidine and morpholine found in urine; pyridine and triethyl amine found in kitchen and garbage odors; and short chain fatty acids, such as 3-methyl-3-hydroxyhexanoic acid, 3-methylhexanoic acid or 3-methyl-2-hexenoic acid, found in axilla malodors. Compounds which have been found in the axilla are described for example by Zeng, et al. ((1991) *J. Chem. Ecol.* 17:1469-1492).

Malodor counteractants or masking agents have been described in the art. For example, sulfhydryl reactants, such as diethyl fumarate, di-n-butyl maleate and N-ethylmaleimide are disclosed in U.S. Pat. No. 5,601,809 as compounds that are effective against axillary malodor. Further, the use of certain aromatic unsaturated carboxylic acid esters in combination with alkyl fumarates as malodor counteractants is disclosed in U.S. Pat. No. 6,610,648. U.S. Pat. No. 6,403,075 addresses fragrance materials with a phenyl ring moiety as ammonia masking agents. Similarly, US 2002/0058017 describes cis-3-hexenol to mask ammonia. Moreover, U.S. Pat. No. 7,585,833 describes methods for formulating fragrances to mask malodor present in products containing ammonia and substituted amines (U.S. Pat. No. 6,379,658, U.S. Pat. No. 6,376,741, U.S. Pat. No. 5,769,832, and U.S. Pat. No. 5,037,412).

Although the art describes compositions and methods for neutralizing certain malodors, there still remains a need for additional compounds that are more efficient against malodors and have a relatively low impact on the olfactive character of a fragrance.

SUMMARY OF THE INVENTION

The present invention is a consumer, industrial, textile, flavor or food product containing a compound selected from the group of Compound 1, Compound 2, Compound 3, Compound 4, Compound 5 or Compound 6. In some embodiments, the consumer, industrial, textile, flavor or food product further includes a fragrance. In other embodiments, the consumer, industrial, textile, flavor or food product is a room freshener spray, a fragrance diffuser, a candle, a sachet, a clothes deodorant, a detergent, a fabric softener, a fabric refresher, a linen spray, a disposable diaper, a diaper pail deodorant, an antiperspirant, a deodorant, a garbage bag, a car freshener, a pet care product, an animal litter material, a fine fragrance, gum, candy, confectionery, or food packaging. A method of counteracting a malodor in air space or a substrate by introducing to an in air space or a substrate a malodor counteracting effective amount of a compound selected from the group of Compound 1, Compound 2, Compound 3, Compound 4, Compound 5 or Compound 6 is also provided, as is a compound having the structure of Compound 3, Compound 4, or Compound 5.

DETAILED DESCRIPTION OF THE INVENTION

Compounds having high-coverage, low-odor properties have now been identified. These compounds have superior malodor coverage and relatively low impact on the olfactive character of a fragrance. Accordingly, this invention is a high-coverage, low-odor compound and use of the same in compositions and methods for counteracting a malodor in air space or a substrate. The compound of the invention has one of the following structures:

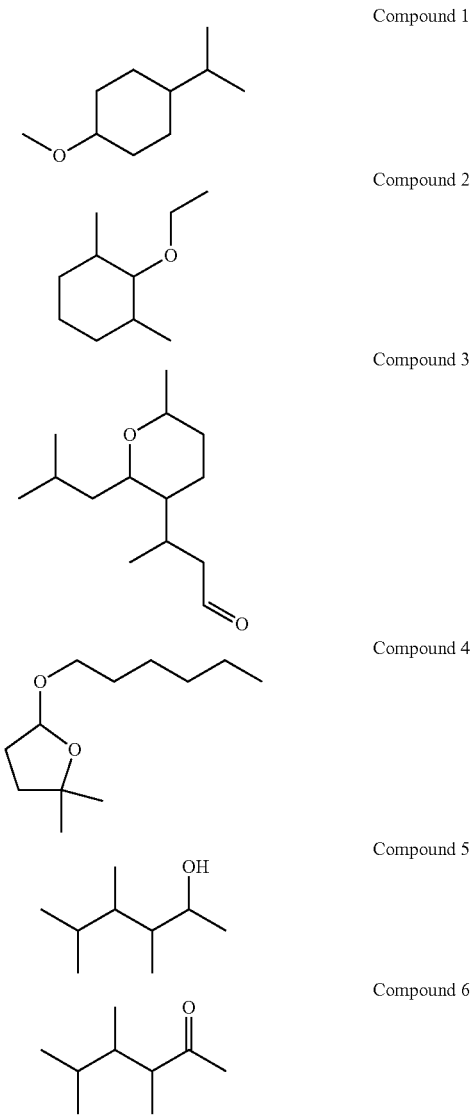

Compound 1

Compound 2

Compound 3

Compound 4

Compound 5

Compound 6

In one embodiment, the compound of the invention is Compound 2 (2-ethoxy-1,3-dimethyl-cyclohexane; CAS No. 286472-48-8). In another embodiment, the compound of the invention is Compound 4 (5-(hexyloxy)-2,2-dimethyl-tetrahydrofuran). In other embodiments, the compound of the invention is Compound 1 (1-methoxy-4-(methylethyl) cyclohexane; CAS No. 112548-32-0), Compound 3 (3-[6-methyl-2-(2-methylpropyl)tetrahydro-2H-pyran-3-yl]butanal), Compound 5 (3,4,5-trimethylhexan-2-ol) or Compound 6 (3,4,5-trimethyl-2-hexanone; CAS No. 79996-76-2).

The malodor counteractant compounds of the present invention can be produced as described herein or by methods known in the art for producing the same or similar compounds to those disclosed herein. For example, Compound can be prepared by the addition of isopropylmagnesium chloride to 3-methyl-3-penten-2-one (Lachance & Eastham (1981) *Can. J. Chem.* 59:2621-2628). Likewise, Compound 2 can be synthesized by known methods (see, Obata, et al. (2000) *Internat. J. Pharmaceut.* 198:191-200). Alternatively, a malodor counteractant compound of the invention can be isolated and purified from a biological source. For example, Compound 1 can be obtained from the root of *Glycyrrhiza glabra* (Kameoka & Nakai (1987) *J. Agricult. Chem Soc. Japan* 61:1119-1121).

Given that the compounds of this invention can be added to products without impacting the olfactory character of the products, the compounds of the invention find use as additives to consumer, industrial, textile, flavor or food products to reduce the concentration of malodors in the headspace of the product. Thus, this invention provides a composition, in particular a consumer, industrial, textile, flavor or food product, that includes Compound 1, Compound 2, Compound 3, Compound 4, Compound 5 and/or Compound 6 as an additive. As used herein, an additive refers to a substance added to a product, wherein the substance is not naturally found in the product. In this respect, the compound of the invention is typically synthesized, isolated and/or purified and subsequently added to the product. In certain embodiments, the purity of the compound is at least 80%, 85%, 90%, 91%, 92%, 93%, 94%, 95%, 96%, 97%, 98%, 99% or 100%.

In most instances, the composition further includes a fragrance ingredient. Fragrances of use in combination with the malodor counteractant compound of the invention include, but are not limited to, individual fragrances, any combination of fragrance oils, essential oils, plant extracts or mixture thereof. Exemplary fragrances include, but are not limited to:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z) 1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H—)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-1-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert-butyl-(2,4-dimethyl-3-cyclohexen-1-yl)ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl) propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1, 16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin;

xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, cistus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom; and xxvii) mixtures thereof.

Alternatively, or in addition to, the malodor counteractant compounds of the invention can be combined with each other and/or other malodor counteractant compounds, e.g., as described in U.S. Pat. No. 7,993,633; US 2013/0101544; US 2013/0101545 and US 2012/0294821.

The malodor counteractant compounds of the invention can be used in a variety of forms and in a variety of products. Advantageously, particular compounds of the present invention (i.e., Compound 3 and Compound 6) are reactive against potent malodor ingredients while not affecting the odor of a fragrance or final product. Thus, in certain embodiments, the present invention features a method for counteracting a malodor by introducing or adding one or more malodor counteractant compounds to an air space (e.g., the surrounding environment) or a substrate so that the malodor of the product is counteracted. The malodor counteractant compounds can be used alone or provided in the form of a consumer, industrial, textile, flavor or food product. As such, the compounds, products, and methods of the invention can be pursued in any situation where malodor is present.

For the purposes of the present invention, a compound counteracts a malodor if it measurably (either qualitatively or quantitatively) reduces the perception or intensity of a malodor. In particular embodiments, a malodor counteractant compound of the present invention reduces the perception or intensity of an isolated malodor by 50-100% as compared to the malodor in the absence of the malodor counteractant compound. When the malodor counteractant compound is used in combination with a fragrance, the fragrance can result in a further reduction in the perception or intensity of a malodor. In particular embodiments, a malodor counteractant compound of the invention reduces the perception or intensity of a malodor by at least 50, 55, 60, 65, 70, 75, 80, 85, 90, 95 or 100% as compared to the malodor in the absence of the malodor counteractant compound.

Malodors particularly targeted by the compounds of the invention include malodors such as bathroom odors, sweat, food odors, textile odors, home care and personal care product base odors, adhesive odors, and paint odors. Thus, the compounds of the invention can be used in products including, but not limited to, air refreshers, fabric refresheners, bar soaps, perfumes, fragrances, cologne, bath or shower gels, shampoos or other hair care products, cosmetic preparations, body odorants, deodorants, antiperspirants, liquid or solid fabric detergents or softeners, bleach products, disinfectants or all-purpose household or industrial cleaners, food, or industrial or textile products such as adhesives, paints, coatings, or textiles.

The composition of the invention can be in the form of an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towelettes, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processing, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, subways and transport systems, and in food applications such as gum, hard candy, confectionery, food packaging, etc. In addition, the malodor counteractant compound can be used in a fine fragrance composed of the malodor counteractant compound and a fragrance.

The composition of the invention is usually one in which the malodor counteractant compound is present together with a carrier by means of which, or from which, the malodor counteractant compound can be introduced into air space wherein the malodor is present, or a substrate on which the malodor has been deposited. For example, the carrier can be an aerosol propellant such as a chlorofluoromethane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant compound is present on a fibrous substrate. In still other embodiments, a composition of the invention also includes a fragrance selected from those described herein.

In some embodiments, the malodor counteractant is encapsulated in a core-shell microcapsule. Encapsulation of active materials is known in the art, see for example U.S. Pat. Nos. 2,800,457, 3,870,542, 3,516,941, 3,415,758, 3,041,288, 5,112,688, 6,329,057, and 6,261,483. Wall forming materials include polyurethane, polysiloxanes, polyurea, polyamide, polyimide, polyvinyl alcohol, polyanhydride, polyolefin, polysulfone, polysaccharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, microcapsules can be made via the simple or complex coacervation of gelatin. Preferred encapsulating polymers include those formed from gelatin, urea-formaldehyde, melamine-formaldehyde, isocyanates, silica, or hydrogel-forming polymers.

Aminoplasts.

A representative process used for aminoplast encapsulation is disclosed in U.S. Pat. No. 3,516,941, though it is recognized that many variations with regard to material and process steps are possible. A representative process used for gelatin encapsulation is disclosed in U.S. Pat. No. 2,800,457, though it is recognized that many variations with regard to material and process steps are possible. Both of these processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB GB2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde Capsules.

Urea-formaldehyde and melamine-formaldehyde precondensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or copolymers. Methods for formation of such melamine-formaldehyde and urea-formaldehyde pre-condensates are set forth in U.S. Pat. No. 3,516,846, U.S. Pat. No. 6,261,483, and Lee et al. (2002) *J. Microencapsulation* 19:559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

Polyurea Capsules.

Polyurea capsules are also well-known in the art. For example, isocyanate-based capsule wall technologies are disclosed in WO 2004/054362; EP 0 148149; EP 0 017 409 B1; U.S. Pat. No. 4,417,916, U.S. Pat. No. 4,124,526, U.S. Pat. No. 5,583,090, U.S. Pat. No. 6,566,306, U.S. Pat. No. 6,730,635, WO 90/08468, WO 92/13450, U.S. Pat. No. 4,681,806, U.S. Pat. No. 4,285,720 and U.S. Pat. No. 6,340,653.

Suitable isocyanates of use in this invention include, for example, 1,5-naphthylene diisocyanate, 4,4'-diphenylmethane diisocyanate (MOI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

To facilitate wall formation, polyurea capsules can also include cross-linking agents, such as amines or alcohols. Examples of amines of particular use include guanidine amines/salts, amphoteric amines, diamines or a combination thereof.

Water soluble diamines are one class of amines of use in this invention as the amine is usually present in the aqueous phase. One class of such amine is of the type:

H$_2$N(CH$_2$)$_n$NH$_2$, where n is ≥1. When n is 1, the amine is a diamine, ethylene diamine. When n is 2, the amine is diamine propane and so on. Exemplary amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are the polyalykylene polyamines of the type:

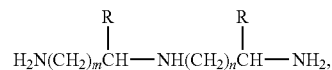

where R equals hydrogen or —C$_3$, m is 1-5 and n is 1-5, e.g., diethylene triamine, triethylene tetraamine and the like. Exemplary amines of this type include, but are not limited to diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

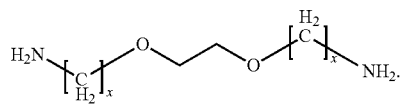

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl) ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, L-arginine, L-lysine monohydrochloride, arginine monohydrochloride and ornithine monohydrochloride.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176 (where x=3) (from Huntsman). Other polyether amines include the JEFFAMINE ED Series, and JEFFAMINE TRIAMINES.

Alcohols of use as cross-linking agents typically have at least two nucleophilic centers. Exemplary alcohols include, but are not limited to, ethylene glycol, hexylene glycol, pentaerythritol, glucose, sorbitol, and 2-aminoethanol.

In another embodiment of the invention, a microcapsule composition is provided that contains an active material that is encapsulated by a polyurea polymer which are reacted in the presence of a capsule formation aid, e.g., a surfactant or dispersant. Classes of protective colloid or emulsifier of use as surfactants or dispersants include maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide, ethylenediamine and ethylene oxide, polyvinylpyrrolidone, polyvinyl alcohols, carboxymethyl cellulose, fatty acid esters of polyoxyethylenated sorbitol and sodium dodecylsulfate.

Commercially available surfactants include, but are not limited to, sulfonated naphthalene-formaldehyde condensates such as MORWET 0425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Typically, hydrocolloids are used to improve the colloidal stability of the slurry against coagulation, sedimentation and creaming. As such, such processing aids can also be used in conjunction with the microcapsules of this invention. As used herein, the term "hydrocolloid" refers to a broad class of water-soluble or water-dispersible polymers having anionic, cationic, zwitterionic or non-ionic character. Hydrocolloids useful for the sake of the present invention include polycarbohydrates, such as starch, modified starch, dextrin, maltodextrin, and cellulose derivatives, and their quaternized forms; natural gums such as alginate esters, carrageenan, xanthanes, agar-agar, pectins, pectic acid, and natural gums such as gum arabic, gum tragacanth and gum karaya, guar gums and quaternized guar gums; gelatin, protein hydrolysates and their quaternized forms; synthetic polymers and copolymers, such as poly(vinyl pyrrolidone-co-vinyl acetate), poly(vinyl alcohol-co-vinyl acetate), poly ((met)acrylic acid), poly(maleic acid), poly(alkyl(meth) acrylate-co-(meth)acrylic acid), poly(acrylic acid-co-maleic acid) copolymer, poly(alkyleneoxide), poly(vinylmethylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like, and their quartenized forms.

Silica/Sol-Gel Capsules.

Sol-gel precursors, i.e., starting compounds capable of forming gels, suitable for the purposes of the invention are known in the art. Sol-gel precursors usable in accordance with the invention are, for example, compounds that are capable of forming gels including, e.g., silicon, boron, aluminum, titanium, zinc, zirconium and vanadium. The precursors can also include metal alkoxides and diketonates. Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof. One example of sol-gel precursors suitable for the purposes of the invention are alkoxysilanes corresponding to the following general formula: $(R_1O)(R_2O)M(X)(X')$, wherein M is Si, Ti, or Zr; X is equal to hydrogen, or —$OR_3$; X' is equal to hydrogen, or —$OR_4$; and $R_1$, $R_2$, $R_3$ and $R_4$ independently represent an organic group, more particularly a linear or branched alkyl group, preferably a $C_{1-12}$ alkyl.

Hydrogels.

Hydrogel capsules can be produced, e.g., by the methods described in PCT/US2013/050054. The polymerizable material used in the preparation of the hydrogel capsules of this invention is typically a monofunctional or multifunctional acrylic or methacrylic acid, or ester thereof. Such compounds are known and can be used in various proportions as blends or mixtures. Representative monofunctional monomers which can be employed according to this invention include but are not limited to acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate. Representative ester monomers of methacrylic acid, which can be used include 2-hydrox ethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino) ethyl methacrylate, 2-(diethylamino)ethyl methacrylate, 2-(diisopropylamino)ethyl methacrylate, N-(2-aminoethyl) methacrylamide hydrochloride, 2-aminoethyl methacrylate hydrochloride, N-(3-aminopropyl)methacrylamide hydrochloride, 2-(tert-butylamino)ethyl methacrylate and the like. The above monomers may be employed separately or in various mixtures according to this invention.

The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetracrylate, bisphenol A dimethacrylate, di(trimethylolpropane) tetraacrylate (DTTA), 1-(acryloyloxy)-3-(methacryloyloxy)-2-propanol (AWE)), trimethylolpropane ethoxylate triacrylate (TPETA), dipentaerythritol pentaacrylate, hexane diacrylate, poly (ethylene glycol) dimethacrylate (PEGDMA), and 1,6-hexandiol dimethacrylate (HDDMA), 1,4-butandiol dimethacrylate, 1,3-butandiol dimethacrylate, 1,6-hexandiol diacrylate, 1,4-butandiol diacrylate, 1,3-butandiol diacrylate.

Hydrogel capsules can be produced by (a) providing an aqueous phase, which contains an emulsifier; (b) providing an oil phase, which contains at least one acrylic or methacrylic acid, or ester thereof, a fragrance and a malodor counteractant; (c) emulsifying the aqueous phase of (a) with the oil phase of (b) to produce an emulsion; (d) polymerizing the emulsion to produce a hydrogel capsule with a fragrance or odorant encapsulated therein; and (e) curing the hydrogel capsule.

In certain embodiments the malodor counteractant compound of the invention is provided as a spray-dried composition. Suitable methods for spray drying are provided in, e.g., PCT/US2013/060290. Briefly, the practice involves dispersing and dissolving dry carrier materials (e.g., sugar, sugar derivatives, modified starch, proteins, celluloses, salts, dextrins, gums, sugar alcohols, polyols, peptides, acids, carbohydrates or hydrocolloids) in solvent until free of lumps. The malodor counteractant compound and optional flavor are then added under constant agitation until a homogeneous mixture is obtained. The emulsion may be further subjected to high shear or homogenized to reduce oil droplet size prior to spray drying. Subsequently, the mixture or emulsion is spray-dried using any suitable spray dryer. For example, a spray dryer with a vertical parallel flow function can be used. The spray dryer should be a system with a dehumidifying and drying function. For example, a spray dryer capable of blowing a high volume of desiccated air with a dew point of less than 5° C. is particularly preferable. For a spray dryer with no dehumidifying and drying function, the spray dryer is inevitably arranged with a dry dehumidifier, e.g., a honeycomb-type rotary dehumidifier (e.g., Nichias Corporation or Sweden PROFLUTE Corporation). Suitable spray dryers include the micromist spray dryer and the hybrid granulator series manufactured by Fujisaki Electric Co., Ltd.; the fluidized spray dryer FSD with internal fluid bed as manufactured by Niro Corporation; the fluid granulation spray dryer and L-8 type spray dryer manufactured by Ogawara (Japan); the DL-21 type and GB-21 type spray dryers manufactured by Yamato Scientific Co., Ltd., and Anhydro Spray Bed Dryer manufactured by SPX Corporation. Once dried, desirably the composition contains from about 0% to about 15% water. Preferably, the composition will have a water activity of 0.1 to 0.6, or more desirably 0.2 to 0.5, and most preferably from 0.2 to 0.4 wherein said levels of dryness can be achieved with or without secondary drying.

Malodor counteracting effective amount is understood to mean the amount of the inventive malodor counteractant compound employed in a composition that is organoleptically effective to minimize the perceived intensity of a given malodor present in air space or deposited on a substrate. The exact amount of malodor counteractant compound employed may vary depending upon the type of malodor counteractant, the type of fragrance, the type of the carrier employed, and/or the level of malodor counteractancy desired. In general, the amount of malodor counteractant compound present is the ordinary dosage required to obtain the desired result. Such dosage is known to the skilled practitioner in the art. In a preferred embodiment, when used in conjunction with malodorous solid or liquid products, e.g., soap and detergent, the compound of this invention may be present in an amount ranging from about 0.005 to about 50 weight percent, preferably from about 0.01 to about 20 weight percent, and more preferably from about 0.05 to about 10 weight percent. When used in conjunction with malodorous gaseous products, a compound of this invention may be present in an amount ranging from about 0.2 milligrams (mg) to about 2 grams (g) per cubic meter of air, preferably from about 0.4 mg to about 0.8 g per cubic meter of air, more preferably from about 2 mg to about 0.4 g per cubic meter of air, and even more preferably from about 4 mg to about 0.2 g per cubic meter of air.

The following examples are provided as specific embodiments of the present invention.

Example 1

Perfumery Assessment

The character of the compounds was analyzed and the results of this analysis are presented in Table 1. By this scale, typical fragrance ingredients would be considered to have an intensity rating of 3 suggesting that the disclosed compounds would have relatively low impact.

TABLE 1

| Compound | Character | Fresh Intensity (1 = lowest-3 = highest) |
|---|---|---|
| 1 | Light, camphoraceous, minty, terpineol-like | 2 |
| 2 | Spicy, camphor, fruity, apple | 2 |
| 3 | Buttery, mushroom, chemical | 1 |
| 4 | Sweet, aldehydic, buttery | 2 |
| 5 | Herbal, medicinal, fruity, dirty, etc. | 2 |
| 6 | Herbal, green, metallic, medicinal, etc. | 2 |

In an initial test, panelists reported high malodor coverage (1-5 scale, 5 being the highest possible coverage) for all six compounds (Table 2).

TABLE 2

| Compound* | Mold/Mildew Malodor | Sweat Malodor |
|---|---|---|
| 1 | 4.62 | 4.51 |
| 2 | 4.44 | 4.56 |
| 3 | 4.08 | 4.15 |
| 4 | 4.27 | 4.53 |
| 5 | 4.22 | 4.47 |
| 6 | 4.04 | 4.30 |

*Compound used as 10% solution.

Testing against various malodors was conducted to quantify malodor control efficacy. Trained panelists determined whether there was a reduction in bathroom, mold/mildew, smoke or sweat malodor intensity using the compounds of this invention. The results of this analysis are presented in Table 3.

TABLE 3

| | Percent Reduction of Malodor Intensity[#] | | | |
|---|---|---|---|---|
| Compound* | Bathroom Malodor | Mold/Mildew Malodor | Smoke Malodor | Sweat Malodor |
| 1 | 92 | 88 | 84 | 83 |
| 2 | 90 | 79 | 87 | 90 |
| 3 | 85 | 81 | 82 | 86 |
| 4 | 83 | 74 | 76 | 79 |
| 5 | 92 | 80 | 83 | 85 |
| 6 | 87 | 90 | 84 | 83 |

*Compound used as 10% solution.
[#]A higher number indicates a better reduction in malodor intensity.

Example 2

Synthesis of 2H-Pyran-3-Propanal, Tetrahydro-Beta, 6-Dimethyl-2-(2-Methylpropyl)-[Compound 3]

SCHEME 1

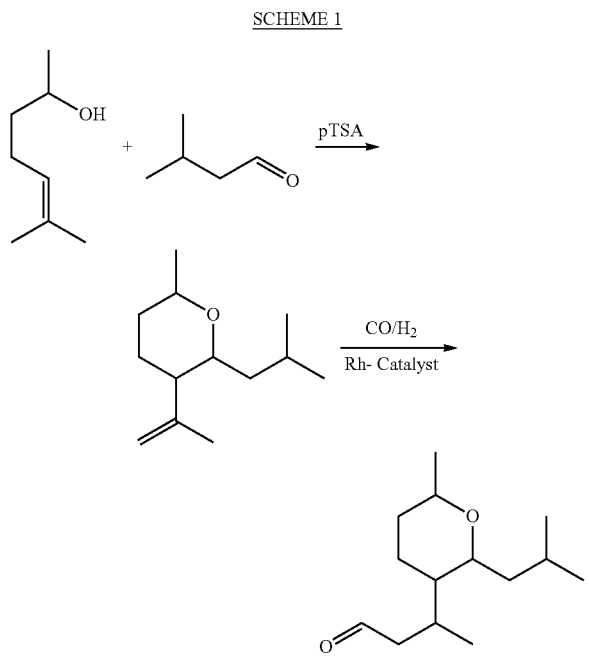

Compound 3 is synthesized in a two-step process starting with Me-Heptenol (IPC 133581)(Scheme 1). In step 1, cyclization of Me-heptenol and isovaleraldehyde is carried out in the presence of acid (pTSA) catalyst in refluxing toluene (temperature ~115-120° C.). An azeotrope is used to remove water. Yields are ~90%. The subsequent oxo reaction is carried out under standard hydroformylation reaction conditions: ~120° C./500 psi Syn gas, and 0.3-1% wt loading of RH 42 catalyst. Reaction gives conversion of ~25-30% after 10-15 hours.

Example 3

Synthesis of 2-Hexanol, 3,4,5-Trimethyl-[Compound 5]

SCHEME 2

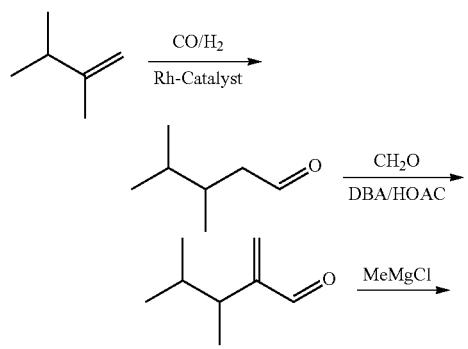

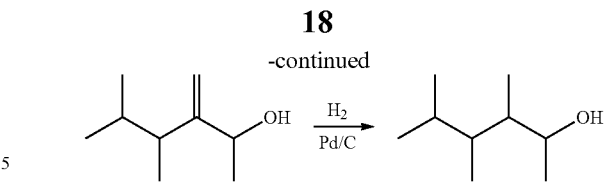

Compound 5 is synthesized in a four step process (Scheme 2) starting from 2,3-dimethyl but-1-ene (DMB-1) purchased from BASF. The first step is an oxo reaction carried out under standard mild oxo conditions: –80° C., 300 psi syn gas, and 0.3% catalyst loading. Conversion after 2-3 hours is 85-90%. The subsequent Mannich reaction includes reaction of the aldehyde with 37% formaldehyde solution in the presence of catalytic Mannich base (dibutyl amine/acetic acid) at 75-80° C. Yield is ~80%. The Grignard reduction involves reaction with methyl magnesium chloride (3.0 M in THF) at 15-30° C. The final hydrogenation step is at 100° C., 400 psi using 5% Pd/C for 5-6 hours.

Example 4

Sugar-Free Stick Gum

A compound of the present invention finds application in a chewing gum, e.g., with a composition as provided in Table 4.

TABLE 4

| Ingredient | Percent (%) | Weight (g) |
|---|---|---|
| Gum Base | 29.84 | 208.88 |
| Sorbitol | 49.00 | 343.00 |
| Sorbitol Syrup 80/55 | 6.06 | 42.42 |
| Mannitol | 5.00 | 35.00 |
| Glycerin | 8.00 | 56.00 |
| Acesulfame K | 0.05 | 0.35 |
| Aspartame | 0.05 | 0.35 |
| Flavor | 2.00 | 14.00 |
| Total | 100.00 | 700.00 |

The gum base is prewarmed and added to a running mixer when softened. A third of the sorbitol is added to the gum base with mixing. During this addition, a small amount of glycerin can be added. Another third of the sorbitol is added along with the sweetener. Subsequently, the balance of glycerin and sorbitol syrup is added with mixing. Flavor and malodor counteractant are incorporated with mixing for three minutes and the balance of sorbitol and mannitol is combined into the final mixture. The mass is mixed an additional 10-15 minutes for uniformity, turned out onto a sheeter dusted with mannitol, and sheeted to the desired size.

Example 5

Hard Candy Preparation

A compound of the present invention finds application in a hard candy, e.g., with a composition as provided in Table 5.

TABLE 5

| IPC | Description | Weight (%) |
|---|---|---|
| 00198863 | Sugar, fine granule | 56.00 |
| 00036480 | Corn Syrup 43 BE | 27.00 |

TABLE 5-continued

| IPC | Description | Weight (%) |
| --- | --- | --- |
| 00230195 | Water | 17.00 |
| | Neat Flavor | variable |

The sugar, syrup, and water are weighed, placed into a 400 mL beaker and stirred together. The ingredients are heated in a 1000 watt microwave until the temperature is approximately 275-280° F. The slurry is allowed to cool to about 235-240° F. before the flavor, malodor counteractant, color, and acids are added. The mixture is blended until uniform, deposited into molds and cooled.

What is claimed is:

1. A consumer, industrial, textile, flavor or food product comprising a compound selected from the group consisting of:

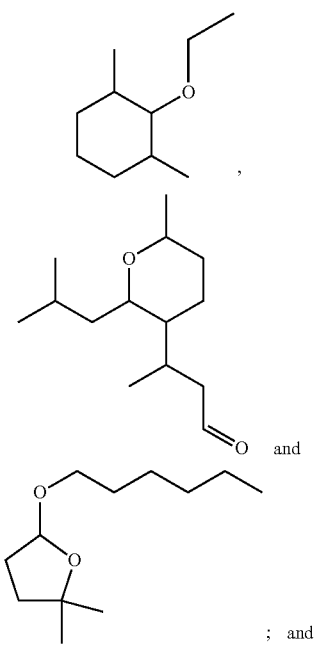

a fragrance.

2. The consumer, industrial, textile, flavor or food product of claim 1, wherein the product is a room freshener spray, a fragrance diffuser, a candle, a sachet, a detergent, a fabric softener, a fabric refresher, a linen spray, a disposable diaper, an antiperspirant, a deodorant, a bar soap, a garbage bag, a car freshener, a pet care product, an animal litter material, fine fragrance, gum, confectionary, or food packaging.

3. A method of counteracting a malodor in an air space or a substrate comprising the step of introducing to the air space or the substrate a consumer, industrial, textile, flavor or food product comprising a compound selected from the group consisting of:

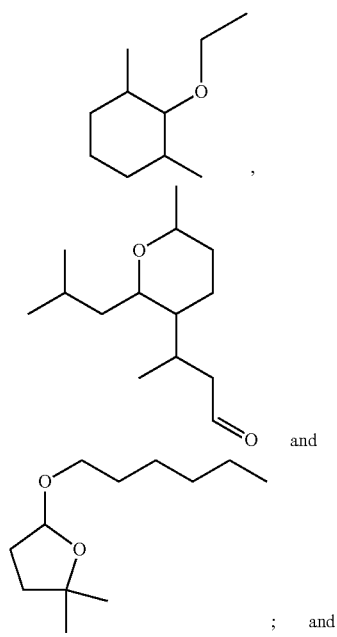

a fragrance.

4. The method of claim 3, wherein the compound is provided at a malodor counteracting effective amount.

5. A compound having a structure of:

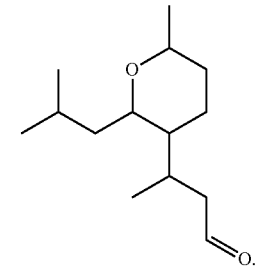 [SMILES: CC(C)CC1OC(C)CCC1C(C)CC=O]

6. The method of claim 4, wherein the malodor counteracting effective amount is from about 0.005 to about 50 weight percent of the substrate.

7. The method of claim 4, wherein the malodor counteracting effective amount is from about 0.01 to about 20 weight percent of the substrate.

8. The method of claim 4, wherein the malodor counteracting effective amount is from about 0.05 to about 10 weight percent of the substrate.

9. The method of claim 4, wherein the malodor counteracting effective amount is from about 0.2 milligrams to about 2 grams per cubic meter of air in the air space.

10. The method of claim 4, wherein the malodor counteracting effective amount is from about 0.4 milligrams to about 0.8 grams per cubic meter of air in the air space.

11. The method of claim 4, wherein the malodor counteracting effective amount is from about 2 milligrams to about 0.4 grams per cubic meter of air in the air space.

12. The method of claim 4, wherein the malodor counteracting effective amount is from about 4 milligrams to about 0.2 grams per cubic meter of air in the air space.

* * * * *